(12) United States Patent
Farqué et al.

(10) Patent No.: US 9,535,039 B2
(45) Date of Patent: Jan. 3, 2017

(54) ACOUSTIC TRANSMITTER AND METHOD FOR UNDERWATER PIPELINE INSPECTION GAUGES

(71) Applicant: Control Devices, Inc., Broken Arrow, OK (US)

(72) Inventors: Jason Farqué, Tulsa, OK (US); Eric Farqué, Tulsa, OK (US)

(73) Assignee: Control Devices, Inc., Broken Arrow, OK (US)

( * ) Notice: Subject to any disclaimer, the term of this patent is extended or adjusted under 35 U.S.C. 154(b) by 318 days.

(21) Appl. No.: 14/266,513

(22) Filed: Apr. 30, 2014

(65) Prior Publication Data

US 2015/0316196 A1    Nov. 5, 2015

(51) Int. Cl.
| | |
|---|---|
| *G01M 3/00* | (2006.01) |
| *G01N 29/04* | (2006.01) |
| *F17D 5/06* | (2006.01) |
| *G01S 3/802* | (2006.01) |
| *G01S 5/18* | (2006.01) |
| *G01S 11/14* | (2006.01) |
| *F16L 55/48* | (2006.01) |

(52) U.S. Cl.
CPC ............. *G01N 29/04* (2013.01); *F17D 5/06* (2013.01); *G01S 3/8022* (2013.01); *G01S 5/18* (2013.01); *G01S 11/14* (2013.01); *F16L 55/48* (2013.01); *G01N 2291/2636* (2013.01)

(58) Field of Classification Search
CPC ..... G01M 3/005; G01M 99/0008; F16L 55/48
USPC .................................... 73/865.8, 865.9, 587
See application file for complete search history.

(56) References Cited

U.S. PATENT DOCUMENTS

| | | | |
|---|---|---|---|
| 2,520,959 A | * | 9/1950 | Powers ..................... C08F 2/24 |
| | | | 524/458 |
| 2,601,248 A | | 6/1952 | Brenholdt |
| 2,820,959 A | | 1/1958 | Bell |
| 3,593,256 A | | 7/1971 | Gannon et al. |
| 3,706,096 A | | 12/1972 | Hammack |

(Continued)

FOREIGN PATENT DOCUMENTS

| | | |
|---|---|---|
| CN | 101567727 A | 10/2009 |
| CN | 101377259 B | 6/2010 |

(Continued)

OTHER PUBLICATIONS

Jason A. Farque; "Digital Offshore Acoustic Pig Tracking with Multipath Robustness"; Pigging Products & Services Association; Jan. 1, 2013; pp. 1-7; US.*

(Continued)

*Primary Examiner* — Lisa Caputo
*Assistant Examiner* — Nigel Plumb
(74) *Attorney, Agent, or Firm* — Dennis D. Brown; Brown Patent Law, P.L.L.C.

(57) ABSTRACT

A multiple frequency ping transmitter which can be carried by a pig which is used in an underwater pipeline. The ping transmitter produces a ping chord which includes a plurality of different tone frequencies which are simultaneously transmitted in the ping chord. Procedures are also provided wherein the multiple frequency ping transmitter is used in a system and method for located a pig which is stuck in the underwater pipeline or for determining the relative velocity of a moving pig.

22 Claims, 8 Drawing Sheets

(56) References Cited

U.S. PATENT DOCUMENTS

| | | | |
|---|---|---|---|
| 4,187,491 A | 2/1980 | Lindstrum et al. | |
| 4,350,984 A | 9/1982 | Fisher | |
| 4,428,073 A | 1/1984 | Verburgt | |
| 4,590,799 A * | 5/1986 | Brown | F16L 55/48 |
| | | | 15/104.063 |
| 4,857,851 A | 8/1989 | Anderson et al. | |
| 4,905,211 A | 2/1990 | Mackelburg et al. | |
| 5,301,167 A | 4/1994 | Proakis et al. | |
| 5,417,112 A * | 5/1995 | Rosenberg | G01B 7/003 |
| | | | 324/207.22 |
| 5,485,148 A * | 1/1996 | Tseng | G01F 1/66 |
| | | | 340/10.41 |
| 5,530,357 A | 6/1996 | Cosman et al. | |
| 5,546,359 A | 8/1996 | Aarseth | |
| 5,651,638 A | 7/1997 | Heggerud | |
| 6,088,580 A * | 7/2000 | Powlousky | G01V 3/17 |
| | | | 324/228 |
| 6,130,859 A | 10/2000 | Sonnenschein et al. | |
| 6,141,293 A | 10/2000 | Amorai-Moriya et al. | |
| 6,333,699 B1 | 12/2001 | Zierolf | |
| 6,384,738 B1 | 5/2002 | Carstensen et al. | |
| 6,474,165 B1 | 11/2002 | Harper et al. | |
| 6,489,771 B1 * | 12/2002 | Farque | G01V 3/104 |
| | | | 324/207.12 |
| 6,512,720 B1 | 1/2003 | Yang | |
| 6,687,188 B2 | 2/2004 | Yang | |
| 6,710,720 B2 | 3/2004 | Carstensen et al. | |
| 6,759,968 B2 | 7/2004 | Zierolf | |
| 6,980,487 B2 | 12/2005 | Davies et al. | |
| 7,222,549 B2 * | 5/2007 | Abney | F16L 55/48 |
| | | | 73/865.9 |
| 7,269,096 B2 * | 9/2007 | Millikin | G01S 5/28 |
| | | | 367/127 |
| 7,505,367 B2 | 3/2009 | Abdi | |
| 7,821,247 B2 * | 10/2010 | Fagbayi | C23F 13/04 |
| | | | 324/71.1 |
| 8,261,623 B2 * | 9/2012 | Miller | F16L 55/48 |
| | | | 73/865.8 |
| 8,356,518 B2 | 1/2013 | Alleyne et al. | |
| 8,378,667 B2 * | 2/2013 | Miska | F16L 55/48 |
| | | | 324/207.22 |
| 2002/0011124 A1 | 1/2002 | Phipps | |
| 2006/0006875 A1 | 1/2006 | Olsson et al. | |
| 2011/0061681 A1 | 3/2011 | Cassidy | |
| 2011/0103189 A1 | 5/2011 | Paulson | |
| 2011/0139538 A1 | 6/2011 | Hill et al. | |
| 2012/0067126 A1 | 3/2012 | Hartog et al. | |
| 2013/0208768 A1 | 8/2013 | Song et al. | |
| 2014/0092709 A1 | 4/2014 | Miller et al. | |

FOREIGN PATENT DOCUMENTS

| | | |
|---|---|---|
| CN | 101251588 B | 5/2011 |
| CN | 201845087 U | 5/2011 |
| CN | 202018515 U | 10/2011 |
| CN | 202057808 U | 11/2011 |
| CN | 102315883 A | 1/2012 |
| CN | 202110294 U | 1/2012 |
| DE | 10338952 | 3/2005 |
| DE | 10338950 | 6/2005 |
| EP | 0122704 | 10/1984 |
| GB | 1285769 | 8/1972 |
| GB | 1397541 | 6/1975 |
| GB | 2297666 | 7/1996 |
| GB | GB2437547 | 10/2007 |
| JP | 08105905 | 4/1996 |
| JP | 2000088561 | 3/2000 |
| JP | 2006003110 A | 1/2006 |
| KR | 100590452 B1 | 6/2006 |
| WO | WO 99/25070 | 5/1999 |
| WO | WO 2007/020475 A1 | 2/2007 |
| WO | WO 2009155708 A1 | 12/2009 |
| WO | WO 2011/161468 A2 | 12/2011 |
| WO | WO 2014043580 A2 | 3/2014 |

OTHER PUBLICATIONS

Baker Hughes, "Vertiline", Wireline-conveyed MFL inspection services reduces pipeline maintenance and rehabilitation costs; Baker Atlas; Published: US.

Zalesak, Joseph F. and Rogers, Peter H., "Low-frequency radiation characteristics of free-flooded ring transducers with application to a low-frequency directional hydrophone"; Oct. 4, 1974; J. Acoust. So. Am, vol. 56, No. 4; Published US.

Giancarlo, et al., "Pipeline acoustic monitoring"; 2012; 7th Pipeline Technology Conference 2012; Published: US.

"Sub-Bottom Profilers" CommTech Tutorial Series; Published: US.

Song, et al.; "Multichannel combining and equalization for underwater acoustic MIMO channels"; 2008; IEEE; Published: US.

Blackmon, et al.; "Performance Comparison of RAKE and Hypothesis Feedback Direct Sequence Spread Spectrum Techniques for Underwater Communication Applications"; Published: US.

Johnson, et al.; "Improved Doppler Tracking and Correction for Underwater Acoustic Communications"; Published: US.

Stonjanovic; Recent Advances in High-Speed Underwater Acoustic Communications; IEEE Journal of Oceanic Engineering; vol. 21, No. 2; Apr. 1996; Published: US.

Catipovic, et al.; "Development of Underwater Modems and Networks"; Oceanography, vol. 6, No. 3; 1993; Published: US.

"Deep Water Acoustic Positioning" IMCA; Oct. 2009; Published: US.

"OnlinE GRID [Gauging Run Integrity Data] System"; OnLine Electronics, Ltd.; 2008; Published: UK.

"OnLinE smart pingers" OnLine Electronics, Ltd.; 2008; Published: UK.

Blair, Gordon; "TDW SMARTTRACK System Revolutionizes Pig Tracking by using Two-Way, Through Wall Communication between the Transponder and Receiver"; TDW Offshore; Published: UK.

"Spy Pig Tracker—Electronic Pig Tracking and Locating Systems Essential to Every Pigging Job"; Published: US.

"Low Frequency Transmitters PNT" Internet Printout: http://ww.aprodit.ru/Aprodit-PNT-en.html; Published: Russia.

Extended European Search Report for European Application No. 15163585.1; Sep. 18, 2015; Europe.

* cited by examiner

ACOUSTIC TRANSMITTER AND METHOD FOR UNDERWATER PIPELINE INSPECTION GAUGES

FIELD OF THE INVENTION

The present invention relates to acoustic transmitters for use in underwater pipelines and also relates to systems and methods for locating and tracking pipeline inspection gauges (i.e., pipeline "pigs") used in underwater pipelines.

BACKGROUND OF THE INVENTION

Oil and gas pipelines require routine maintenance. A substantial part of this maintenance involves the deployment of pipeline "pigs"—typically bullet-shaped foam or flexible urethane devices—that pass through the pipeline while pressing against the pipeline wall. The pigs can remove both solid and liquid buildup from the pipeline to increase the flow and the efficiency of the pipeline, and to help in controlling and monitoring corrosion.

However, a continuing need exists for faster, more accurate, and more cost effective devices and systems for locating and tracking pigs used in pipelines. While traveling through a pipeline, a pig will sometimes become stuck. The consequences of a pipeline pig becoming stuck in a pipeline due to, for example, a dent in the pipeline, an out-of-round shape of a segment of the pipeline, a partially closed in-line valve, or other reasons can be difficult and costly to address.

There are a variety of prior art methods used for tracking pigs within pipelines. One method involves attaching an electromagnetic transmitter to the pig and then using an electromagnetic receiver on the outside of the pipeline to detect the electromagnetic signal and locate the pig. Another approach has involved attaching an acoustic pinger to the pig and then using an acoustic receiver on the outside of the pipeline to detect and locate the source of the acoustic signal.

Acoustic pipeline pig tracking is used in offshore, subsea, and other underwater pipelines. This is because the relatively low frequency and low energy signals generated by an acoustic pinger do not propagate well within a gaseous media. Because of this limitation, acoustic pig tracking systems require that the pipeline be located within a liquid medium (e.g., sea or lake water) and typically further require that the pipeline also be filling with a liquid medium (e.g., crude oil, refined liquid hydrocarbon products, etc.).

While acoustic pig tracking systems are only useful for underwater tracking, they have distinct advantages for use in such applications. Foremost among these advantages is range. While electromagnetic tracking systems typically have a range of only a few tens of meters, acoustic pig tracking systems can detect the presence of an underwater pipeline pig from several kilometers away. This advantage would be significant if it could be utilized to reduce or eliminate the need to deploy divers or remote operated vehicles (ROVs) to monitor the progress and location of the pig.

Heretofore, the acoustic pig tracking transmitters carried by underwater pipeline pigs have transmitted a ping signal which has consisted of only a single frequency tone. This tone varies by manufacturer and pinger but is typically in the range of from 8 kHz to 40 kHz. An acoustic receiver is used shipside to listen for this single tone and to downshift the signal into the range of human hearing. This type of acoustic pinger can be likened to ringing a bell wherein the single ping tone is emitted repeatedly.

One significant shortcoming of the prior art single tone transmitter and system is that the signal can be severely degraded, distorted, or even lost entirely due to multipathing. Multipathing is produced by the tone being reflected in the underwater environment by (a) the sea bottom, (b) the water surface, (c) thermoclines, and (d) other underwater surfaces presented, for example, by natural topographic formations, work vessels, oil platforms, etc. In addition, noise from the environment and from work vessels and ROVs can overlap with and obscure or cancel out the frequency of interest without warning.

Figure 1:
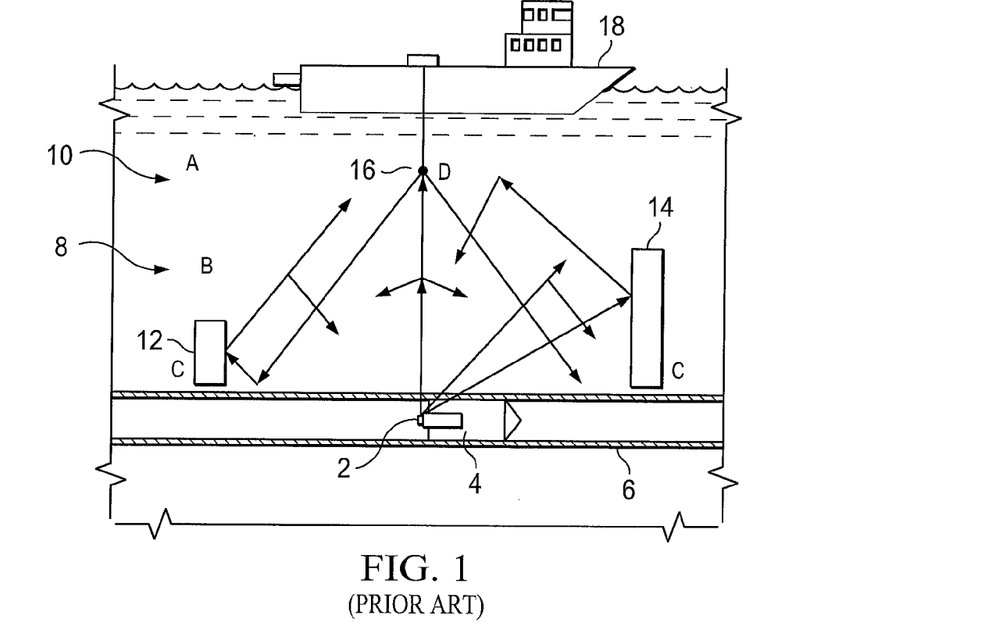
FIG. 1 schematically illustrates the occurrence of multipathing when using a prior art acoustic pinger 2 which transmits only a single tone.

The multipathing behavior of a single tone underwater signal emitted from a prior art transmitter 2 installed in a pipeline pig 4 is illustrated in FIG. 1. The pig 4 is located within a liquid pipeline 6. The acoustic pinger 2 within the pipeline 6 transmits acoustic energy into the surrounding water. Some portion of the acoustic energy is reflected by thermoclines 8 and 10 in the water. Additionally, subsea structures 12 and 14 reflect the signal as well.

Each of these reflections splits the acoustic energy and ultimately delays the arrival of some portion of the energy at the receiver (i.e., a hydrophone) 16 carried by the surface vessel 18. Moreover, as the energy arrives from the multipath sources, its phasing has an additive and subtractive effect on the total amount of acoustic energy received by the hydrophone.

Consequently, due to the effect of multipathing, it is possible to be quite near the acoustic source 2 and yet not receive a reliable signal, or to detect a signal which seems to "come and go". This significantly reduces the trustworthiness and reliability of the system. Also, another deficiency of the single tone systems is that very little information may conveyed by the single frequency, and the reliability of the information received is no better than the reliability of the single tone by which it is carried.

Therefore, a need exists for an improved acoustic transmitter and system for locating and tracking pipeline pigs used in underwater pipelines. The improved acoustic transmitter and system will preferably (a) significantly reduce or eliminate the effects of multipathing, (b) provide highly accurate and rapid location and tracking of pigs in underwater pipelines, (c) significantly reduce or eliminate the need to use divers and/or remote operated vehicles (ROVs) for pig locating and tracking operations, and (d) provide the ability to transmit significantly more information regarding the status or condition of the pig and the pipeline. In addition, the improved acoustic transmitter and system will preferably also be capable of (1) determining the relative speed of a moving pipeline pig, (2) accurately determining the estimated point location of the pipeline pig rather than simply determining that the pipeline pig and transmitter are within a sphere of detection, and (3) continuously tracking a moving pig from a moving surface vessel, without the need for divers and ROVs.

SUMMARY OF THE INVENTION

The present invention satisfies the needs and alleviates the problems discussed above.

In one aspect, there is provided a ping transmitter comprising a housing and a free-floating ring transducer which projects from said housing. The free-floating ring transducer transmits a ping chord comprised of a plurality of different frequencies wherein the plurality of different frequencies are transmitted simultaneously in the ping chord.

In another aspect, there is provided a pipeline pig apparatus comprising a pipeline pig and a ping transmitter carried by the pipeline ping. The ping transmitter comprises a housing and a free-floating ring transducer which projects from the housing. The free-floating ring transducer transmits a ping chord comprised of a plurality of different frequencies wherein the plurality of different frequencies are transmitted simultaneously in the ping chord.

In another aspect, there is provided a method of locating or tracking a pig in an underwater pipeline comprising the step of transmitting from a ping transmitter carried by the pig a ping chord comprised of a plurality of different frequencies wherein the plurality of different frequencies are transmitted simultaneously in the ping chord.

In another aspect, there is provided a method of locating or tracking a pig in an underwater pipeline comprising the step of receiving, using a receiving system carried by a surface vessel, a ping chord transmitted by a ping transmitter carried by the pig, the ping chord comprising a plurality of different frequencies wherein the plurality of different frequencies are transmitted simultaneously in the ping chord.

Further aspects, features, and advantages of the present invention will be apparent to those of ordinary skill in the art upon examining the accompanying drawings and upon reading the following Detailed Description of the Preferred Embodiments.

DETAILED DESCRIPTION OF THE PREFERRED EMBODIMENTS

Figure 2:
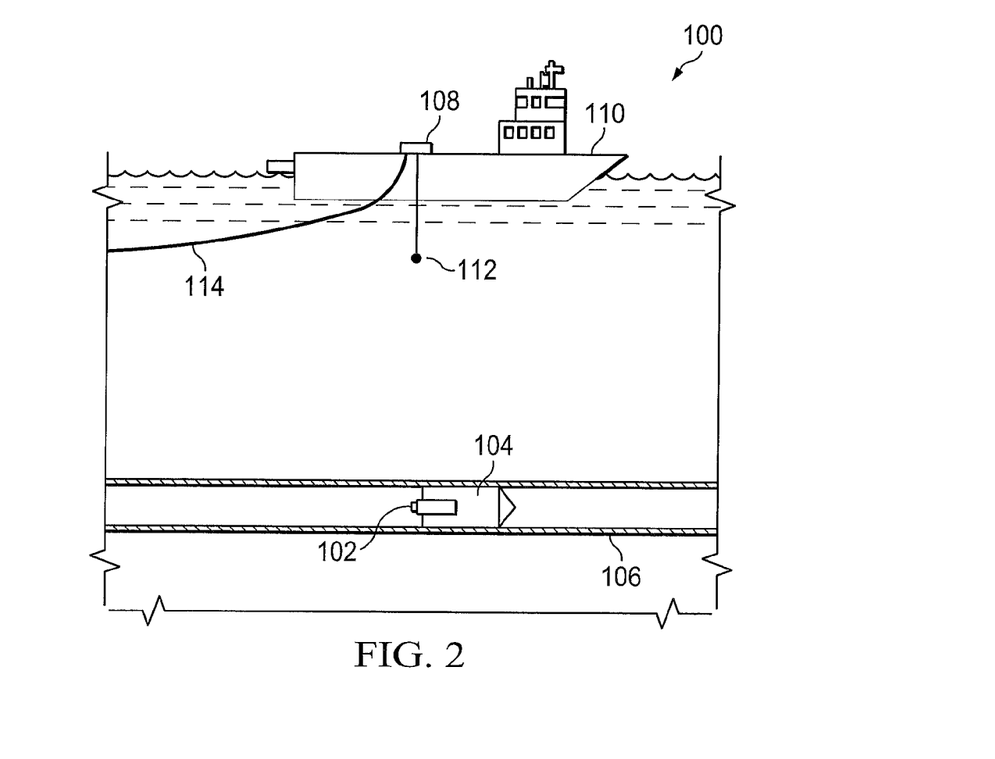
FIG. 2 schematically illustrates an embodiment 100 of an acoustic tracking system 100 provided by the present invention.
Figure 3:
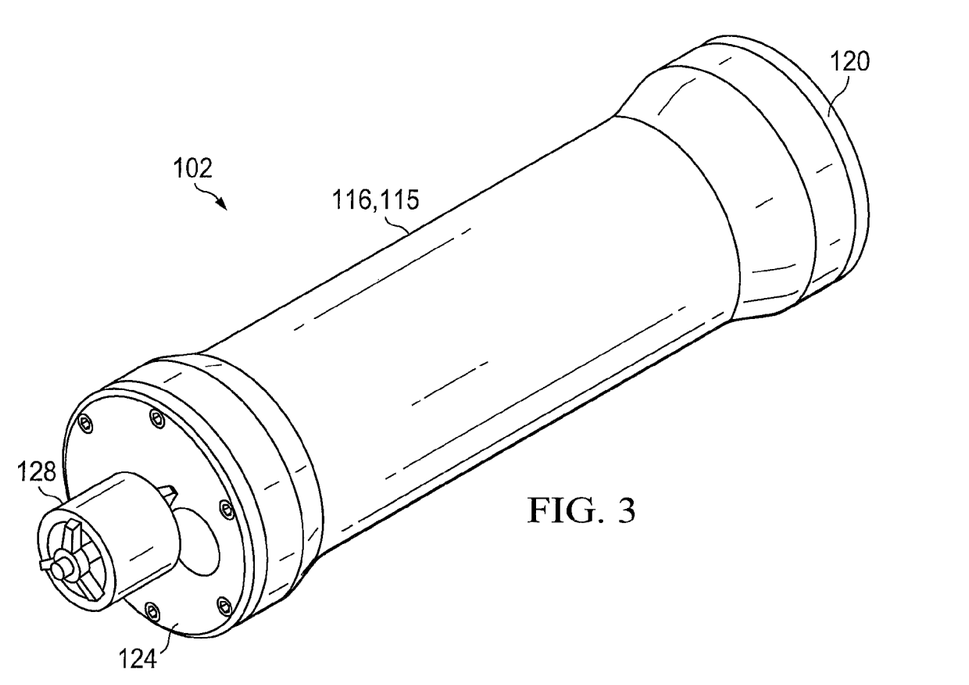
FIG. 3 is a perspective view of an embodiment 102 of a multiple frequency ping transmitter provided by the present invention.
Figure 4:
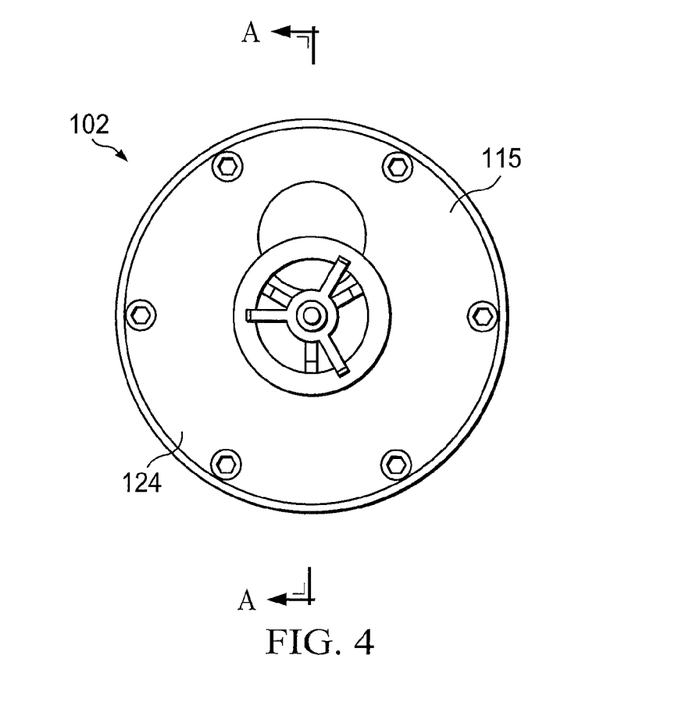
FIG. 4 is an elevational leading end view of the inventive multiple frequency ping transmitter 102.
Figure 5:
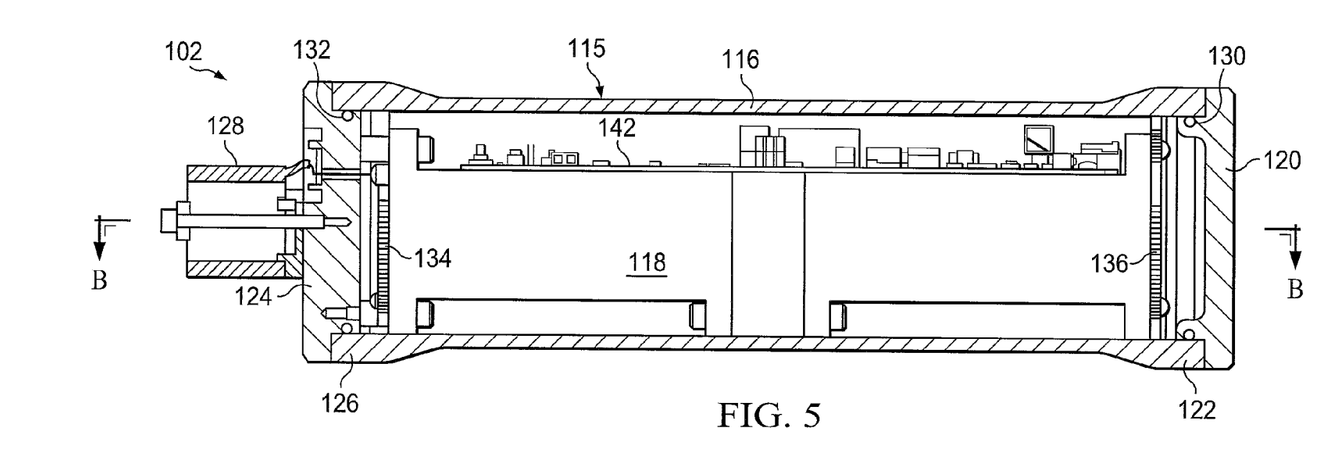
FIG. 5 is a cutaway elevational side view of the inventive multiple frequency ping transmitter 102 as seen from perspective A-A shown in FIG. 4.
Figure 6:
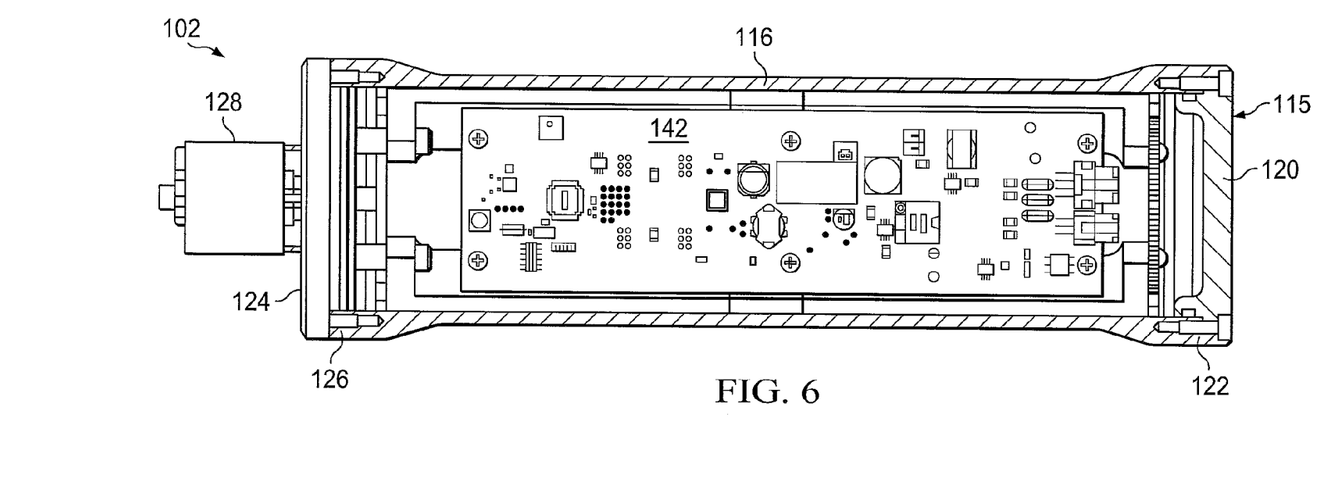
FIG. 6 is a cutaway top view of the inventive multiple frequency ping transmitter 102 as seen from perspective B-B shown in FIG. 5.

An embodiment 100 of the acoustic tracking system provided by the present invention is illustrated in the FIG. 2. The inventive tracking system preferably comprises: an inventive multiple frequency acoustic ping transmitter 102 which is carried by (e.g., attached to, pulled by, pushed by, or otherwise conveyed by) a pipeline pig 104 in an underwater pipeline 106; an inventive deck box 108 located on board a surface ship 110; and an omnidirectional hydrophone 112 and/or a towable hydrophone 114 carried by the surface ship 110.

As illustrated in FIGS. 3-6, the inventive multiple frequency acoustic ping transmitter 102 preferably comprises: an exterior pressure housing 115 which includes a housing tube 116; a battery holder 118 positioned within the housing tube 116 for holding one or a plurality of batteries for powering the transmitter 102; a housing end cap or other pressure closure 120 which is removably attached to one of the longitudinal ends (preferably the leading end) 122 of the housing tube 116 for inserting, removing, and replacing the batteries; another housing end cap or other pressure closure 124 removably installed on the other longitudinal end (preferably the trailing end) 126 of the housing tube 116; a free-flooding ring transducer 128 which is installed in and projects axially outward from the exterior of the trailing end cap 126 of the housing 115; O-ring seals 130 and 132 for sealing the leading and trailing end caps 120 and 124; positive and negative battery terminals 134 and 136 within the housing tube 116 at the longitudinal ends of the battery holder 118; and a circuit board 142 within the housing tube 116 which carries the microcontroller and other electronics for operating the inventive pinger 102.

The inventive multiple frequency acoustic ping transmitter 102 creates acoustic multi-frequency tones (chords) by vibrating the free flooding ring (FFR) transducer 128, said FFR transducer 128 being in direct contact with the surrounding liquid medium within the pipeline 106. The FFR transducer 128 is preferably a ceramic toroidal FFR transducer.

Figure 7:
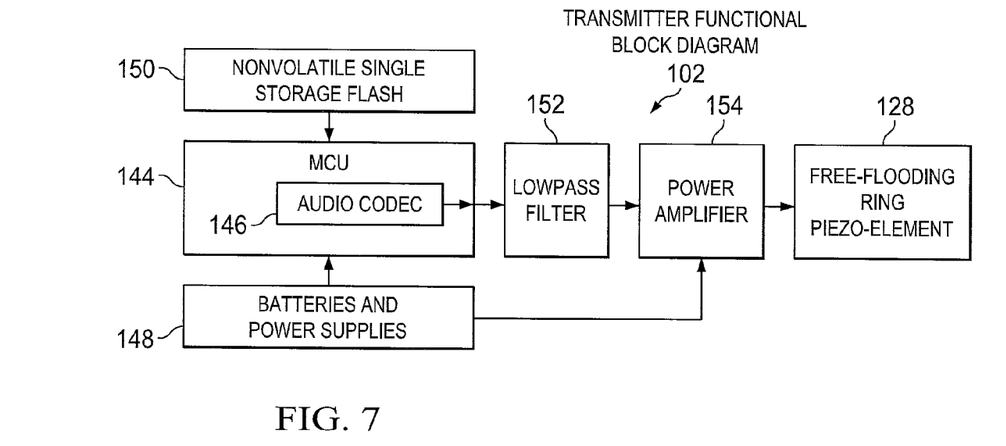
FIG. 7 is a functional block diagram of the inventive multiple frequency ping transmitter 102.

As seen in the block diagram provided in FIG. 7, the electronic operating system of the inventive multiple frequency ping transmitter 102 preferably comprises: a microcontroller unit (MCU) 144 which includes audio codec program software 146 and is powered by the system batteries 148; a nonvolatile signal storage flash 150 which is linked to the MCU 144; a lowpass filter 152 which is linked to the MCU 144; and a power amplifier 154 which is powered by the system batteries 148 and is linked between the lowpass filter 152 and the free-flooding ring transducer 128.

Figure 8:
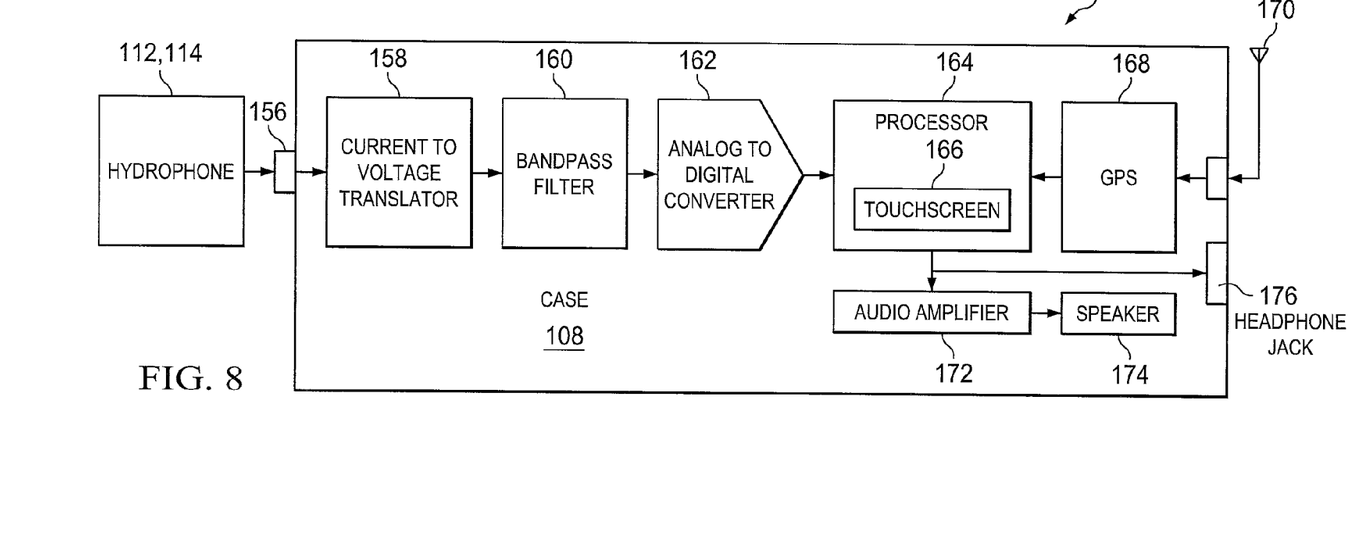
FIG. 8 is a functional block diagram of an embodiment 108 of a deck box receiver provided by the present invention.

The deck box 108 located on board the surface ship 110 is a computerized system which receives and processes the signals captured by the omnidirectional hydrophone 112 or towable hydrophone 114 and presents them to an operator. As illustrated in FIG. 8, the deck box 108 preferably comprises: a hydrophone connector 156; a current to voltage translator 158 which is linked to the hydrophone 112 or 114 via the hydrophone connector 156; a bandpass filter 160 which is linked to the current to voltage translator 158; an analog to digital converter 162 which is linked to the bandpass filter 160; a computer processor 164 which receives the digital signal from the analog to digital converter 162; a touchscreen or other interface 166 which is included in or linked to the computer processor 164; a GPS locator 168 which is linked to the computer processor; a GPS antenna 170; an audio amplifier 172 and speaker 174 which are linked to the processor 164; and a headphone jack 176 which is also linked to the computer processor 164. The deck box 108 and processor 164 preferably also have USB upload and download capability.

The inventive acoustic tracking system 100 overcomes the problems of multipathing, signal loss, and obfuscation by utilizing a chord comprising a plurality of, preferably 15, simultaneous frequencies within a single ping transmitted by the ping transmitter 102. The 15 frequencies used to build the ping "chords" preferably vary between 9 kHz and 11 kHz. The receiver software contained in the deck box 108 continually scans the environment for, records and separates these 15 frequencies through the use of a Fast Fourier Transform. While the strength of some of these tones may be weakened to the point of destruction by the environment, most of the tones are received.

In this regard, the shipside deck box receiver 108 can be tuned to accommodate the loss of an allowable number of tones, with the default preferably being three. In other words, if an acoustic signal is received which matches 12 or more of the individual tones of a valid 15 tone chord, the signal will be regarded as a valid signal from the inventive ping transmitter 102. The loss of as many as three single tones within a chord would be tolerated.

The use of a multi-frequency ping in the inventive tracking system 100 overcomes the adverse effects of multipathing. When the inventive ping transmitter 102 emits a chordal ping, each of the 15 different frequency tones within the chord has a different transmission coefficient. As these frequencies are reflected and refracted at the interfaces between mediums with differing transmission velocities, each constituent frequency reflects and refracts slightly differently than its neighboring frequency. Because of this effect, known as Snell's Law, the arrival of some, if not all, of the chord's 15 frequencies is certain to occur.

In addition, the inventive chord transmission system also allows for the construction of an acoustic alphabet. The microcontroller unit (MCU) 144 within the inventive ping transmitter 102 preferably carries a plurality of unique chords, each representing, for example, a different character of an alphabet. This enables the MCU 144 of the inventive ping transmitter 102 to respond to various different conditions, occurrences, and changes in its environment by making a corresponding change in the chord transmitted.

Since each chord is unique, small amounts of digital information represented by changes in the chords can be transmitted and reliably conveyed from the ping transmitter 102 to the shipside deck box receiver 108. The transmitted chords can be used, for example, to uniquely identify the pig 104, send pressure and temperature information, respond to physical damage (e.g., gauge plate damage), shocks or vibration, etc. As will be understood by those in the art, pressure sensors, temperature sensors, shock and vibration accelerometers, and/or other types of sensors can be included in the inventive acoustic ping transmitter 102 and/or pig 104 to provide all manner of status and operational information.

Because of its GPS receiver 168 and other components, the deck box receiver 108 of the inventive tracking system 100 has the ability to measure Doppler shift in the chords transmitted by the inventive acoustic pinger 102. These Doppler speed measurements allow the inventive tracking system 100 to determine the speed at which the pig 104 is traveling. This information can be used to ascertain whether the pig 104 is stuck in the pipeline 106 or is moving normally. Moreover, because the inventive tracking system 100 can perform these operations without having to deploy ROVs or divers, significant savings are provided in regard to both time and money.

Figure 9:
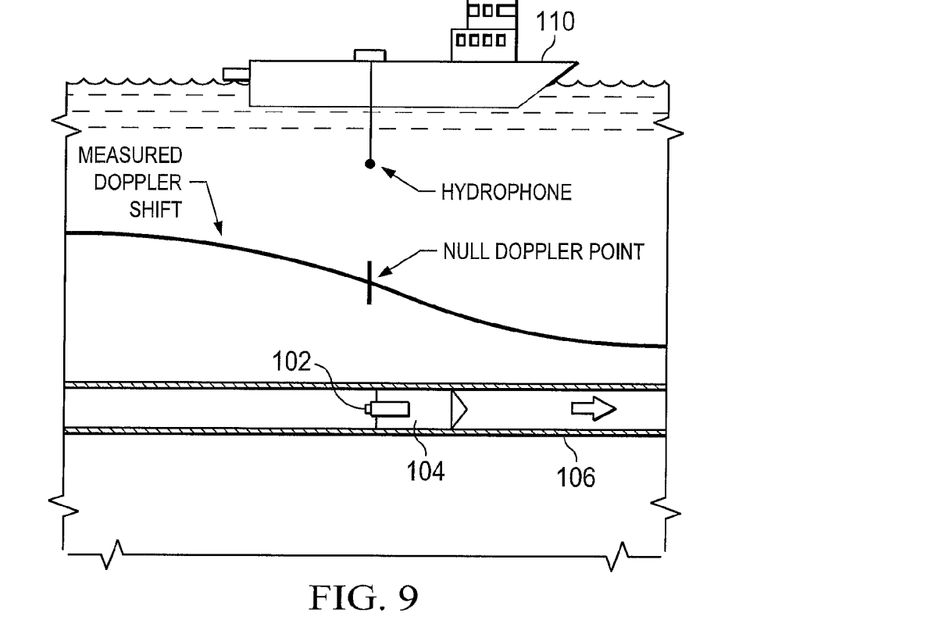
FIG. 9 schematically illustrates an embodiment of the method of the present invention wherein a surface vessel 110 is positioned above an underwater pipeline 106 to detect the arrival of a pig 104 carrying an inventive ping transmitter 102.

In most instances, a pipeline operator or maintenance contractor will have maps showing the location of a pipeline 106 of interest on the sea bottom. In such cases, a surface vessel 110 carrying the inventive tracking system 100 can be positioned at a fixed point above the pipeline to await the arrival of a pig 104 as illustrated in FIG. 9. When Doppler information is measured from the approaching pig 104, it will provide the speed at which the pig 104 is traveling.

As the pig approaches and passes beneath the vessel 110, the measured Doppler shift relative to the vessel 110 will begin to decrease at a rate dependent upon the depth of water at the site. As the pig 104 moves directly beneath the vessel 110, the apparent Doppler of the pig will drop to zero momentarily and then begin to show a downshift in frequencies, indicating that the pig 104 is moving away. Consequently, the speed at which the pig 104 is traveling and the moment that the pig 104 passes directly beneath the vessel 110 are readily ascertained.

On the other hand, if the pig 104 is stuck in the pipeline 106 so that the pig 104 is not moving, it is a simple matter to follow the pipeline 106 with the surface vessel 110 until the chord transmitted from the pig 104 is located. Converse to the example above, the Doppler shift measured by the deck box receiver 108 when the vessel 110 is moving and the pig 104 is stationary will be the speed of the vessel 110 relative to the inventive pinger 102. As when the pig 104 is moving and the vessel 110 is stationary, the moment of null Doppler will coincide with the point at which the vessel 110 passes directly over the pig 104 and can thus be used to mark the location of the stationary pig 104.

The inventive system 100 is also able to ascertain the bearing over sea to a pipeline pig 104 which is stuck in a pipeline 106 when the precise location of the pipeline 106 is not known. This inventive procedure benefits greatly from the multipath resistance provided by the inventive system 100.

In accordance with this inventive procedure, the inventive system 100 can be utilized to find the bearing (direction) to the inventive acoustic ping transmitter 102 which is carried by the pig 104. The first step in this process is for the surface vessel 110 to follow the estimated route of the pipeline 106 listening for ping chords from the inventive pinger 102. For this step, a towable hydrophone 114 is preferably used. The towable hydrophone 114 is resistant to the noise created by the flowing water and is of sufficient length so as to be removed from the noise created by the vessel 110 itself. The towable hydrophone 114 will typically be from 20 to 50 meters in length.

When the deck box system 108 detects the chord transmitted by the ping transmitter 102, the vessel 110 should be brought to a stop and the Doppler of the pig 104 ascertained. Given a stationary vessel 110, the measured Doppler of a stationary (stuck) pig 104 should be zero.

Once it has been verified that the pig 104 is not moving, the vessel 110 should be moved, preferably at a speed of approximately five knots, so that GPS and Doppler information collected by the deck box system 108 on the moving vessel 110 can be logged. In particular, the deck box 108 preferably maintains ongoing measurements of the relative Doppler speed of the pig 108 to determine: (1) whether the vessel 110 is moving away from or toward the pinger 104 (negative or positive Doppler) and (2) the relative speed.

The relative speed measured will not necessarily be the same as the speed of the vessel 110, but may instead be a radial velocity (tangential speed) of the vessel 110 versus the acoustic ping transmitter 102. When the vessel 110 is not moving directly toward or away from the ping transmitter 102 but is instead moving at a tangent with respect to the pinger 102, the measured speed will be some fraction of the vessel's true speed.

Figure 10:
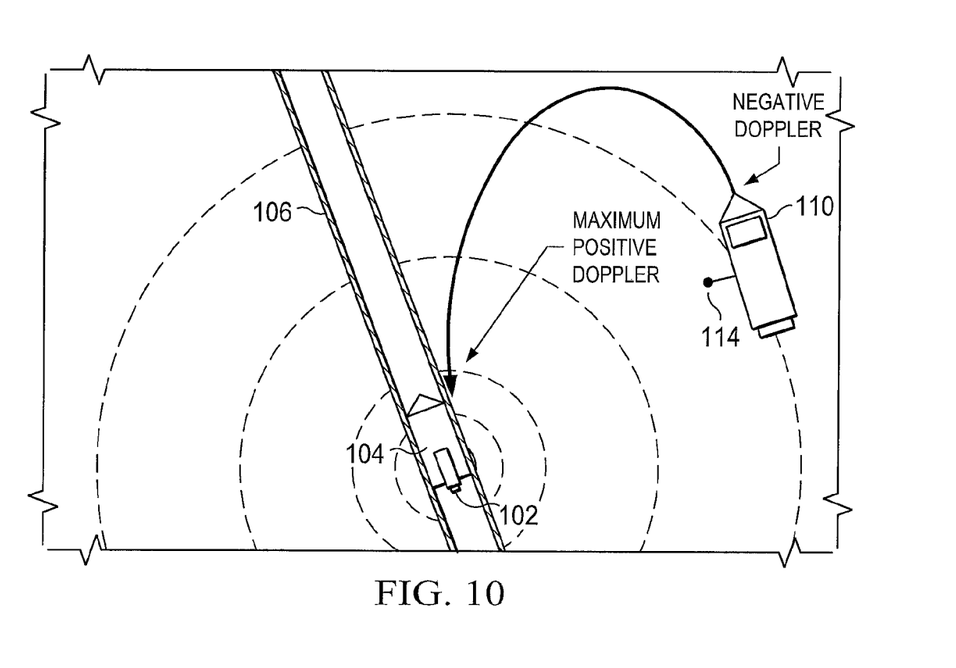
FIG. 10 schematically illustrates another embodiment of the inventive method to determine a bearing to a pig 104 stuck in the underwater pipeline 106.

As illustrated in FIG. 10, once negative or positive Doppler is ascertained, the inventive system 100 knows whether the vessel 110 is moving away from (measured negative Doppler) or toward (measured positive Doppler) the target pinger 102. Unless a positive Doppler is measured and the speed measured by the inventive system matches the true speed of the vessel, the vessel 110 will preferably begin a slow turn and continue the turn while the inventive system 100 watches for a maximum positive Doppler shift. This maximum positive Doppler will identify a direct bearing to the acoustic ping transmitter 102 within the pipeline 106. Once this course is found, the vessel 110 maintains this bearing to the pinger 102 until a null Doppler point (i.e., a flip from positive to negative) is measured, thus indicating that the vessel 110 is directly above the pig 104.

The ability of the inventive system 100 to find the proper bearing to a target as just described based upon the reliable chord signal provided by the inventive chordal ping transmitter 102 is not only very important, but it also represents a significant advance over the capabilities of the prior art. However, even beyond the ability to establish a true course to the target, the inventive system 100 is also able to establish the GPS location of and distance to the ping transmitter 102.

An example of the inventive procedure for determining the location of and distance to a pig 104 which is stuck in a pipeline 116, wherein the location of the pipeline 116 is not precisely know, is illustrated in FIGS. 11-14. In this method, once again, the vessel 110 will preferably proceed along the estimated pipeline route using a towable hydrophone 114 until the acoustic chord transmitted by the inventive ping transmitter 102 is received. When the chord signal is detected, the vessel 110 will preferably stop and the Doppler shift speed of the acoustic ping transmitter 102 will be verified at zero. Once it is confirmed that the pig 104 is in fact stationary, the vessel 110 will begin to move along a circular course 105 or a substantially circular (e.g., an oval or other closed rounded shape) on the water surface, preferably at a speed of about 5 knots, while the deck box system 108 logs GPS and Doppler information.

While traveling along a circular or substantially circular course 105 so that the bearing of the vessel 110 in relationship to the acoustic ping transmitter 102 is continuously changing, the positive/negative Doppler measurements gathered by the inventive system 100 will also change so that, by continuing along this course 105, the inventive system 100 can locate and mark a surface point 180 of maximum positive Doppler shift, a surface point 186 of maximum negative Doppler Shift, and two surface points 182 and 185 of null Doppler Shift. Each of these solutions provides a bearing relative to the acoustic source 102 (as viewed from above) so that, by means of triangulation using two or more of these solutions, the GPS surface location of, and the surface distance to, the pig 104 can be determined.

Figure 11:
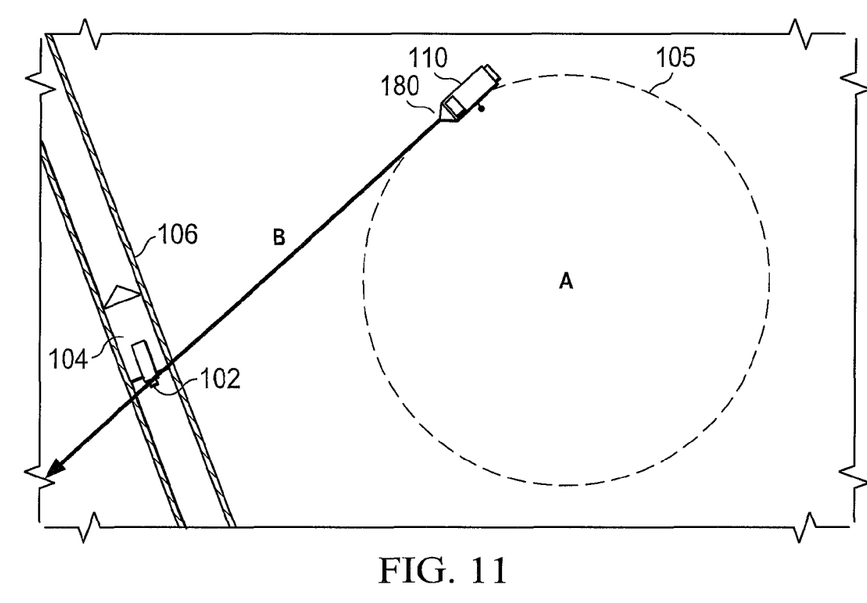
FIG. 11 schematically illustrates a first step of another embodiment of the inventive method to find a bearing B of maximum positive Doppler shift.
Figure 12:
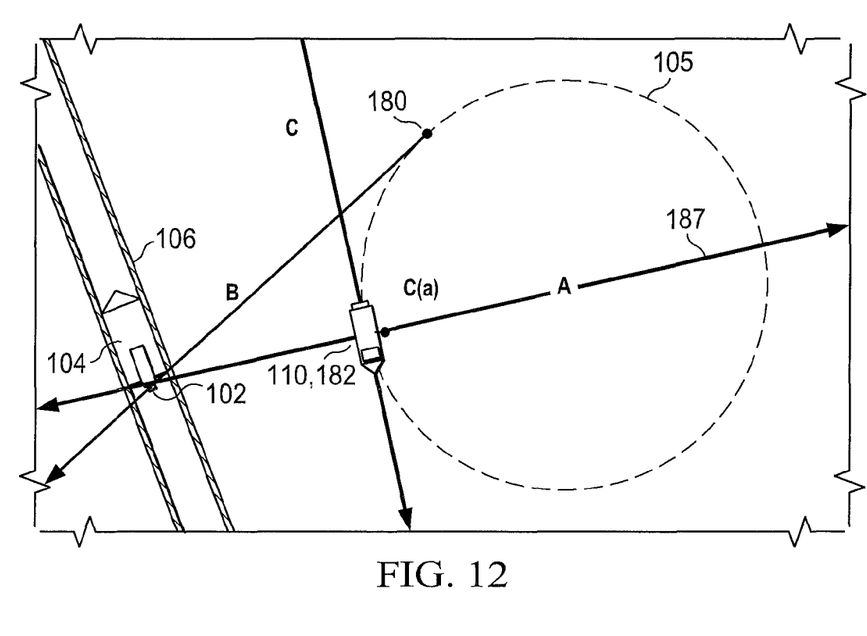
FIG. 12 schematically illustrates a second step of this method to locate a bearing C of null Doppler shift.

When the vessel 110 reaches the point 180 on path 105 of maximum positive Doppler shift, a bearing B from point 180 to the pig 104 is established. Then, when the vessel 110 reaches the null Doppler point 184 on path 105 traveling on bearing C, a line 187 is established which is perpendicular to bearing C and runs through point 184 and the location of the ping transmitter 102. The intersection of line 187 with the previously determined bearing line C provides the surface location above the pig 104.

Figure 13:
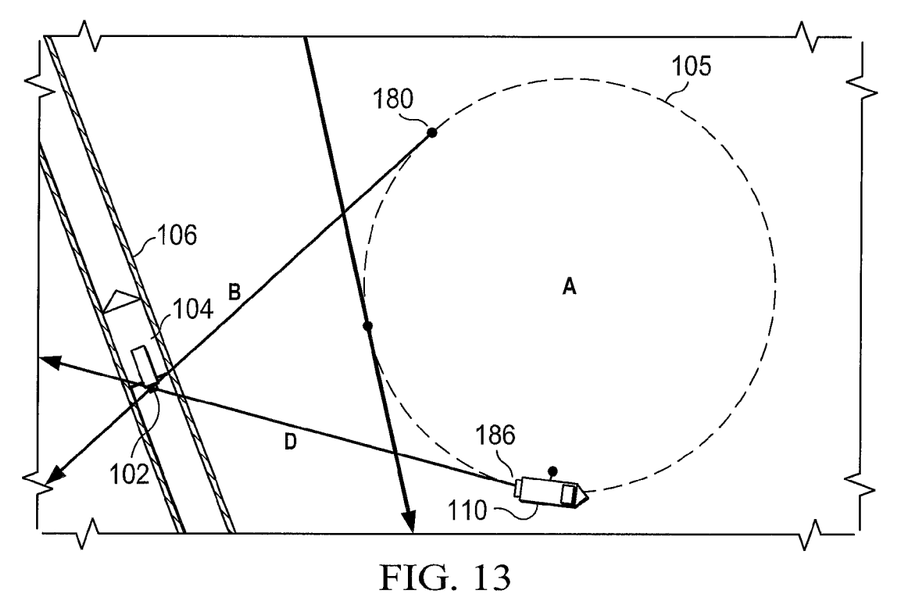
FIG. 13 schematically illustrates a third step of this method to locate a reverse bearing D corresponding to a maximum negative Doppler shift.

Next, when the vessel reaches the point 186 of maximum negative Doppler shift, a reverse bearing D from point 186 back to the acoustic ping transmitter 102 is established such that the intersection of the reverse bearing line D with the bearing line C and/or the line 187 also provides the surface location above the pig 104.

Figure 14:
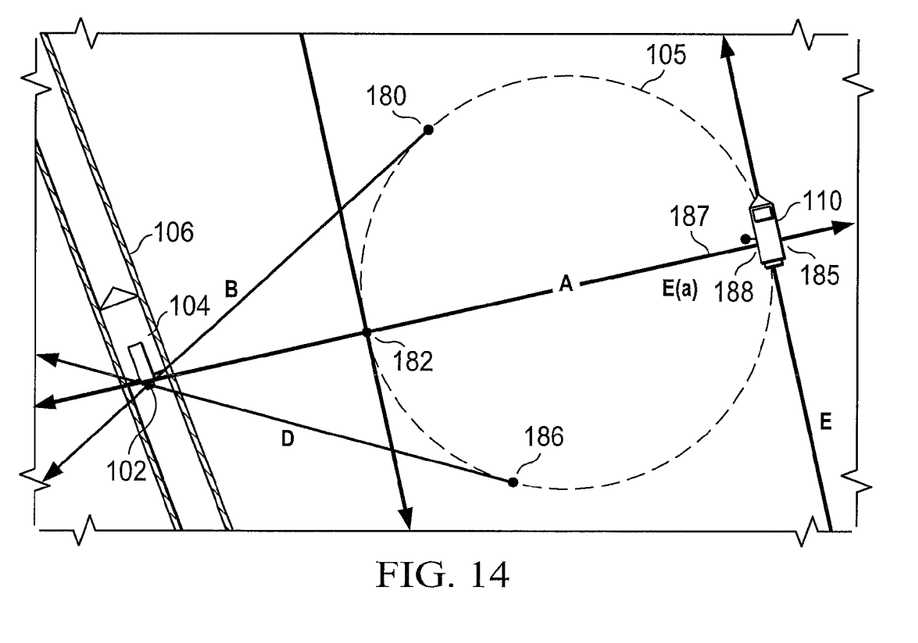
FIG. 14 schematically illustrates a fourth step of this method to locate a second bearing E of null Doppler shift.

Finally, when the vessel 110 reaches the second null Doppler point 188 traveling on bearing E, the perpendicular line 187 which also runs through the first null Doppler point 182 is again established.

As will be apparent, if the method is continued until all of this information is obtained, some of the bearing data constitutes redundant information. However, this redundant information is helpful in that it allows the inventive system 100 to use averaging to improve the accuracy of the triangulation. As the inventive system 100 gathers the Doppler information described above, an increasingly accurate prediction of the surface location above the inventive ping transmitter 102 is obtained based upon the convergence points of the bearings determined.

Consequently, by performing all or a sufficient portion of this procedure, the vessel 110 can navigate to the GPS coordinates provided by the inventive system 100 as indicating the surface location above the pig 4. While navigating toward these coordinates, the inventive system 100 will preferably continue to monitor for (a) the maximum positive Doppler shift, which will confirm the correct course to the target, and (b) the positive to negative Doppler shift which will indicate and confirm that the vessel 110 has arrived at a point which is directly over the pig 104.

In addition to the above, in the case of a pig 104 which is moving in the pipeline 106, because the precise transmission frequencies of the chords of the inventive pinger 102 are known, the inventive system 100 can also be used to obtain a reliable estimate of the radial velocity of the moving pig 104. Moreover, the inventive system can provide this information using only a single receiving hydrophone 114, rather than requiring the deployment of an array.

Figure 15:
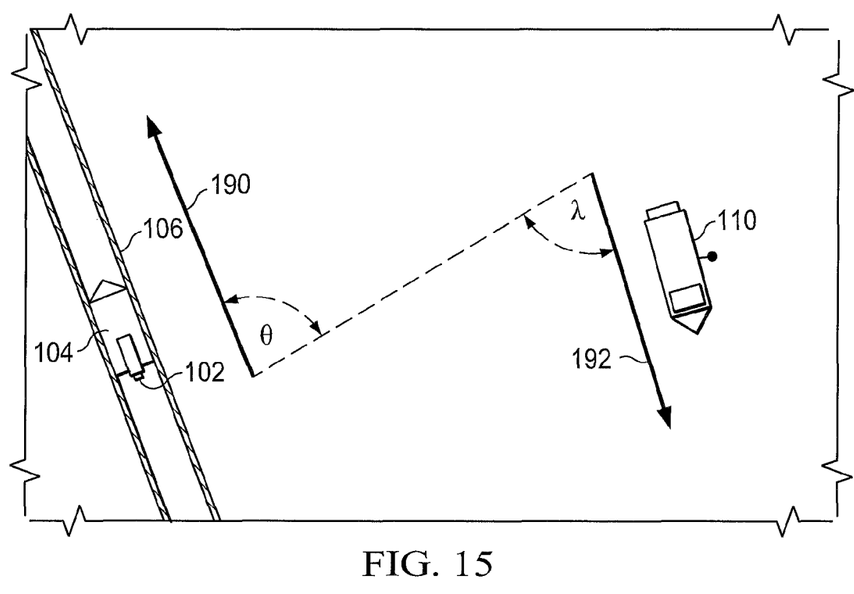
FIG. 15 schematically illustrates another embodiment of the inventive method to determine the relative velocity of a moving pig 104.

For the moving pig 104, FIG. 15 illustrates the geometry that defines the relative Doppler measured at the receiving vessel 110. Relative Doppler depends upon the vector 190 defined by the motion of the transmission source (i.e., the inventive ping transmitter 102) and the vector 192 defined by the motion of the receiving vessel 110. The relationship between the motion of the transmitting pinger 102 and the motion of the receiving vessel 110 is described by the following formula:

$$\text{Doppler} = (\text{Pinger Speed} \times \cos(\theta)) + (\text{Vessel Speed} \times \cos(\lambda))$$

Where Doppler and Vessel Speed are known variables and Pinger Speed, $\lambda$, and $\theta$ are unknown.

With this number of unknown variables, the equation is not solvable with only one data point. However, by either making an assumption regarding the course vector 190 of the ping transmitter 102 (i.e., the course down the pipeline 106), or making course changes of the surface vessel 110 to obtain sufficient additional data, the equation can be solved.

Thus, the present invention is well adapted to carry out the objects and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within this invention as defined by the claims.

What is claimed:

1. A ping transmitter comprising: a housing and a free-floating ring transducer projecting from said housing, wherein said free-floating ring transducer transmits a ping chord comprised of a plurality of different frequencies, said plurality of different frequencies being transmitted simultaneously in said ping chord and said plurality of different frequencies comprising at least 12 different frequencies.

2. The ping transmitter of claim 1 wherein said ping chord comprises fifteen of said different frequencies which are transmitted simultaneously.

3. The ping transmitter of claim 1 wherein said housing includes an end cap and said free-floating ring transducer projects from said end cap.

4. The ping transmitter of claim 1 further comprising a battery holder within said housing.

5. A pipeline pig apparatus comprising: a pipeline pig and a ping transmitter carried by said pipeline ping, said ping transmitter comprising a housing and a free-floating ring transducer projecting from said housing, wherein said free-floating ring transducer transmits a ping chord comprised of a plurality of different frequencies, said plurality of different frequencies being transmitted simultaneously in said ping chord and said plurality of different frequencies comprising at least 12 different frequencies.

6. The pipeline pig apparatus of claim 5 wherein said ping chord comprises fifteen of said different frequencies which are transmitted simultaneously.

7. The pipeline pig apparatus of claim 5 wherein said housing includes an end cap and said free-floating ring transducer projects from said end cap.

8. A method of locating or tracking a pig in an underwater pipeline comprising the step of transmitting from a ping transmitter carried by said pig a ping chord comprised of a plurality of different frequencies, said plurality of different frequencies being transmitted simultaneously in said ping chord and said plurality of different frequencies comprising at least 12 different frequencies.

9. The method of claim 8 wherein said ping chord comprises fifteen of said different frequencies which are transmitted simultaneously.

10. The method of claim 8 wherein said ping transmitter comprises a housing and a free-floating ring transducer projecting from said housing, wherein said ping chord is transmitted from said free-floating ring transducer.

11. The method of claim 8 further comprising the step of receiving said ping chord using a receiving system carried by a surface vessel, said receiving system including a hydrophone.

12. A method of locating or tracking a pig in an underwater pipeline comprising the step of receiving, using a receiving system carried by a surface vessel, a ping chord transmitted by a ping transmitter carried by said pig, said ping chord comprising of a plurality of different frequencies, said plurality of different frequencies being transmitted simultaneously in said ping chord and said plurality of different frequencies comprising at least 12 different frequencies.

13. The method of claim 12 further comprising the steps of stopping said surface vessel and then determining a Doppler speed of said ping chord to determine if said pig is stationary or is moving in said underwater pipeline.

14. The method of claim 12 further comprising the steps of stopping said surface vessel over said underwater pipeline and then determining when said pig passes beneath said surface vessel by measuring a Doppler shift of said ping chord to determine when a null Doppler occurs.

15. The method of claim 12 further comprising the step of determining a bearing line to a location of said pig by moving said surface vessel and changing a course of said surface vessel until a bearing of maximum positive Doppler shift of said ping chord is measured.

16. The method of claim 15 further comprising the steps of:
determining a reverse bearing line to said location of said pig by moving said surface vessel and changing said course of said surface vessel until a bearing of maximum negative Doppler shift is measured and
finding a point of intersection of said bearing line of said bearing of maximum positive Doppler shift and said reverse bearing line of said bearing of maximum negative Doppler shift to determine said location of said pig.

17. The method of claim 16 wherein said course of said surface vessel is changed to find said bearing of maximum positive Doppler shift and said bearing of maximum negative Doppler shift by moving said surface vessel along a substantially circular course.

18. The method of claim 15 further comprising the steps of:
moving said surface vessel and changing said course of said surface vessel until a bearing line at a point of null Doppler shift is determined and
finding a point of intersection of said bearing line of said bearing of maximum positive Doppler shift and a line which is perpendicular to said bearing line at said point of null Doppler shift to determine said location of said pig.

19. The method of claim 18 wherein said course of said surface vessel is changed to find said bearing of maximum positive Doppler shift and said bearing line at said point of null Doppler shift by moving said surface vessel along a substantially circular course.

20. The method of claim 12 further comprising the steps of moving said surface vessel and changing a course of said surface vessel until a bearing line at a point of null Doppler shift of said ping chord is measured.

21. The method of claim 20 further comprising the steps of:
Determining a reverse bearing line to said location of said pig by moving said surface vessel and changing said course of said surface vessel until a bearing of maximum negative Doppler shift is measured and
finding a point of intersection of a line which is perpendicular to said bearing line at said point of null Doppler shift and said reverse bearing line of said bearing of maximum negative Doppler shift to determine said location of said pig.

22. The method of claim 21 wherein said course of said surface vessel is changed to find said bearing line at said point of null Doppler shift and said bearing of maximum negative Doppler shift by moving said surface vessel along a substantially course.

* * * * *

UNITED STATES PATENT AND TRADEMARK OFFICE
CERTIFICATE OF CORRECTION

PATENT NO. : 9,535,039 B2
APPLICATION NO. : 14/266513
DATED : January 3, 2017
INVENTOR(S) : Kerr Page 1 of 1

It is certified that error appears in the above-identified patent and that said Letters Patent is hereby corrected as shown below:

On the Title Page

Item (12) delete "Farqué et al." and insert --Kerr--.

Item (72) Inventors, should read:
--(72) Inventor: Robert R. Kerr, Glasgow (GB)--.

Signed and Sealed this
Twenty-eighth Day of March, 2017

Michelle K. Lee
*Director of the United States Patent and Trademark Office*